United States Patent
Eddy

(10) Patent No.: US 9,433,708 B2
(45) Date of Patent: Sep. 6, 2016

(54) INTRAVENOUS CONNECTOR HAVING ANTIMICROBIAL TREATMENT

(71) Applicant: Patrick E. Eddy, Allendale, MI (US)

(72) Inventor: Patrick E. Eddy, Allendale, MI (US)

( * ) Notice: Subject to any disclaimer, the term of this patent is extended or adjusted under 35 U.S.C. 154(b) by 20 days.

(21) Appl. No.: 14/216,020

(22) Filed: Mar. 17, 2014

(65) Prior Publication Data

US 2014/0276456 A1    Sep. 18, 2014

Related U.S. Application Data

(60) Provisional application No. 61/786,930, filed on Mar. 15, 2013.

(51) Int. Cl.
| | | |
|---|---|---|
| *A61L 29/16* | (2006.01) | |
| *A61L 29/06* | (2006.01) | |
| *A61M 39/26* | (2006.01) | |

(52) U.S. Cl.
CPC ............ *A61L 29/16* (2013.01); *A61L 29/06* (2013.01); *A61M 39/26* (2013.01); *A61L 2300/208* (2013.01); *A61L 2300/404* (2013.01); *A61M 2039/267* (2013.01)

(58) Field of Classification Search
CPC ............ A61L 29/06; A61L 2300/208; A61L 2300/404; A61L 29/16; A61L 2300/606; A61L 29/08; C08L 83/04; A61M 2039/267; A61M 39/26; A61M 1/285; A61M 1/3661; A61M 2025/006; A61M 2202/0021; A61M 2202/0413; A61M 2205/0205; A61M 2210/12; A61M 25/0017; A61M 25/0045
See application file for complete search history.

(56) References Cited

U.S. PATENT DOCUMENTS

| | | |
|---|---|---|
| 5,079,004 A | 1/1992 | Blank et al. |
| 5,428,078 A | 6/1995 | Cohen et al. |
| 5,685,866 A | 11/1997 | Lopez |
| 5,959,014 A | 9/1999 | Liebeskind et al. |
| 6,224,579 B1 | 5/2001 | Modak et al. |
| 6,821,943 B2 | 11/2004 | Avery et al. |
| 7,045,673 B1 | 5/2006 | Batich et al. |
| 7,709,694 B2 | 5/2010 | Batich et al. |
| 7,790,217 B2 | 9/2010 | Toreki et al. |
| 8,025,120 B2 | 9/2011 | Eddy |

(Continued)

FOREIGN PATENT DOCUMENTS

WO    2008097599 A2    8/2008

OTHER PUBLICATIONS

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

*Primary Examiner* — Aradhana Sasan
(74) *Attorney, Agent, or Firm* — Price Heneveld LLP

(57) ABSTRACT

An intravenous connector is provided having a valve body having first end configured to receive a syringe for administering medicine to a patient; a spike element having a tapered hollow spike terminating in a tip at a first end and having a second end configured for attaching to an intravenous tube, the spike element secured in the valve body such that the tip is disposed proximate the first end of the valve body and the second end of the spike element is located at a second end of the valve body; and a pliable seal member disposed in the valve body around the tapered hollow spike and exposed at the first end of the valve body. An antimicrobial material comprising a silane quaternary ammonium salt is incorporated on or within the seal member and is coated on the valve body and the spike element.

15 Claims, 3 Drawing Sheets

(56) References Cited

U.S. PATENT DOCUMENTS

| | | |
|---|---|---|
| 8,491,922 B2 | 7/2013 | Eddy |
| 2007/0042198 A1 | 2/2007 | Schonemyr et al. |
| 2007/0218096 A1 | 9/2007 | Wooley |
| 2008/0260804 A1 | 10/2008 | Morris et al. |
| 2011/0282302 A1* | 11/2011 | Lopez .................. A61M 39/10 604/247 |
| 2012/0173274 A1 | 7/2012 | Rensvold et al. |
| 2015/0352320 A1* | 12/2015 | Eddy ................ A61M 25/0045 604/29 |

* cited by examiner

INTRAVENOUS CONNECTOR HAVING ANTIMICROBIAL TREATMENT

CROSS-REFERENCE TO RELATED APPLICATION

This application claims priority under 35 U.S.C. §119(e) upon U.S. Provisional Patent Application No. 61/786,930, entitled "INTRAVENOUS CONNECTOR HAVING ANTIMICROBIAL TREATMENT" filed on Mar. 15, 2013, by Patrick E. Eddy, the entire disclosure of which is incorporated herein by reference.

BACKGROUND OF THE INVENTION

The present invention generally relates to medical valves and needleless connectors for intravenous (IV) applications, more particularly to IV connectors having one end configured for attaching to an IV tube and another end configured to receive a syringe for administering medicine to a patient.

Needleless IV connectors having valve mechanisms are known in the art, an example of which is the medical valve described in U.S. Pat. No. 5,685,866 assigned to ICU Medical, Inc. who also makes such needleless IV connectors under the trademark MicroClave®. One of the MicroClave® needleless IV connectors is available with an antimicrobial treatment, where the antimicrobial treatment consists of ionic silver. Such ionic silver, however, is subject to leaching over time.

SUMMARY OF THE INVENTION

According to an embodiment of the present invention, an IV connector is provided comprising a valve body having an open first end configured to receive a syringe for administering medicine to a patient; and a silicone seal member disposed in the valve body and exposed at the open first end of said valve body configured to receive the syringe, wherein an antimicrobial material is incorporated on or within the silicone member and is coated on the valve body, wherein said antimicrobial material comprises a silane quaternary ammonium salt.

According to another embodiment of the present invention, a method for making an IV connector having a valve body and a silicone seal member is provided, where the method comprises the steps of providing a silicone slurry including therein an antimicrobial material comprising a silane quaternary ammonium salt, processing the slurry to form the silicone member, and assembling the silicone member and the valve body.

According to another embodiment of the present invention, an intravenous connector is provided comprising: a valve body having an open first end configured to receive a syringe for administering medicine to a patient, and a second end opposite the first end; a spike element having a tapered hollow spike terminating in a tip at a first end and having a second end configured for attaching to an intravenous tube, said spike element secured in said valve body such that said tip is disposed proximate the first end of said valve body and the second end of said spike element is located at the second end of said valve body; and a pliable seal member disposed in said valve body around said tapered hollow spike and exposed at the open first end of said valve body configured to receive the syringe, wherein an antimicrobial material is incorporated on or within said seal member and is coated on said valve body and said spike element, and wherein said antimicrobial material comprises a silane quaternary ammonium salt.

In one or more of these embodiments, the silane quaternary ammonium salt may comprise 3-(trimethoxysilyl) propyldimethyloctadecyl ammonium chloride.

These and other features, advantages, and objects of the present invention will be further understood and appreciated by those skilled in the art by reference to the following specification, claims, and appended drawings.

DETAILED DESCRIPTION OF THE EMBODIMENTS

Figures 1, 2:
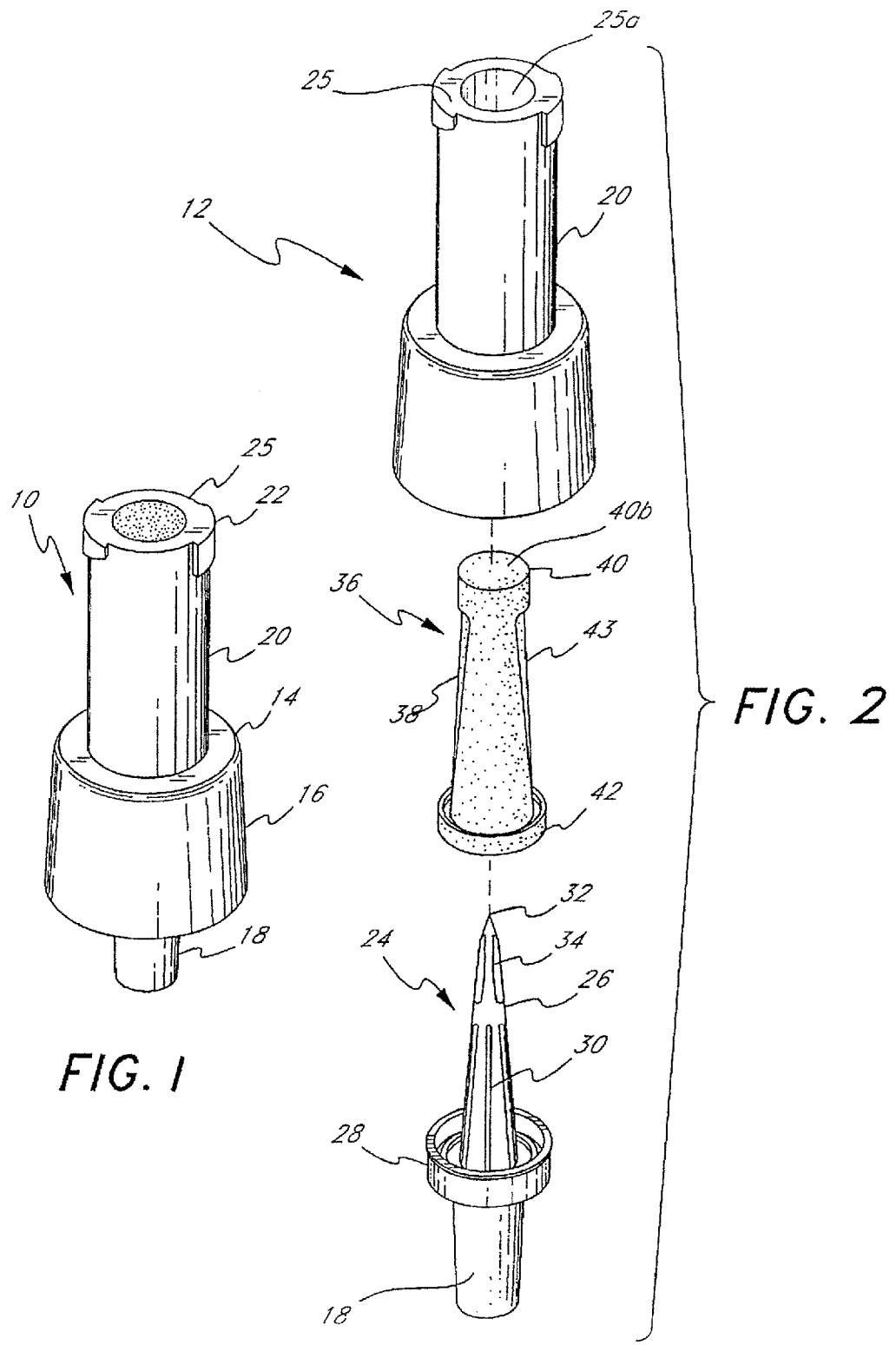
FIG. 1 is a perspective view of a needleless IV connector that may be treated according to one embodiment of the present invention.
FIG. 2 is an exploded perspective view of the valve shown in FIG. 1.
Figure 3:
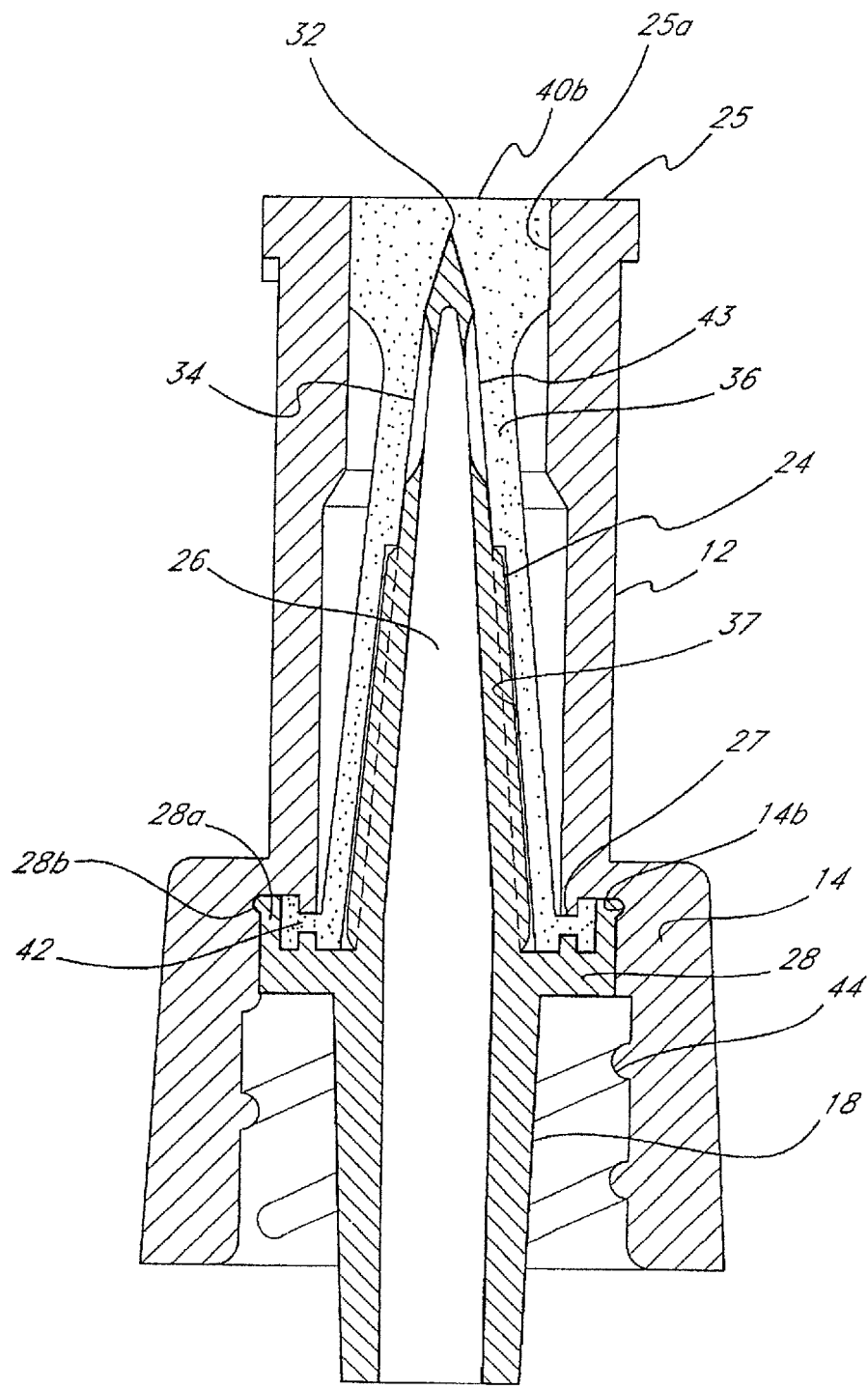
FIG. 3 is a longitudinal cross-sectional view of the assembled valve of FIG. 1.

Reference will now be made in detail to the present preferred embodiments of the invention, examples of which are illustrated in the accompanying drawings. Wherever possible, the same reference numerals will be used throughout the drawings to refer to the same or like parts. In the drawings, the depicted structural elements are not to scale and certain components are enlarged relative to the other components for purposes of emphasis and understanding.

As noted above, the embodiments described herein pertain to IV connectors/ports, with or without valves. Needleless IV connectors are connected to one end of an IV tube or luer and may remain in place for the duration of a patent's stay in the medical facility in which the IV is administered. Such needleless IV connectors may thus be handled by various staff members and may be used to administer numerous dosages of medication or to withdraw fluid. Because such needleless IV connectors provide a path into the patient's bloodstream, it is important that they do not harbor bacteria or other microbes.

A novel needleless IV connector is disclosed herein that not only provides the requisite properties for a needleless IV connector, but also eliminates bacteria on contact. As discussed below, the components of the connector are either treated with or formed with an antimicrobial substance comprising a silane quaternary ammonium salt. One example of a needleless IV connector that may be so treated is shown in FIGS. 1-5, which correspond to FIGS. 1-5 of the aforementioned U.S. Pat. No. 5,685,866, the entire disclosure of which is hereby incorporated herein by reference.

As illustrated, needleless IV connector 10 has a valve body 12, a seal (or septum) 36, and a spike element 24. Valve body 12 includes an upper conduit 20, a skirt 16, an annular ring 14, locking ears 22 (or optionally threads), and an annular lip 25 with an opening 25a. Valve body 12 provides an opening with threads 44 that may engage a cap or other medical device such as a container, IV tube, or luer. Valve body 12 is generally tubular as discussed further below. Valve body 12 may be formed of a thermal plastic.

Seal 36 has a seal cap 40 with a generally flat top surface 40b, a lower lip 42, and a tapered side-wall 38 having a plurality of longitudinal grooves 43 to facilitate compression of the seal. Seal 36 has an opening at the end where the lower lip 42 is located presenting a cavity 37 for receiving spike element 24. The outer dimensions of seal 36 are chosen to allow seal 36 to be inserted within the inside of valve body 12. Seal 36 may be formed of silicone or some other pliable material.

Spike element 24 includes a hollow spike 26 terminating at a tip 32 at one end and an inner conduit 18 at the other end. An annular cuff 28 is positioned between hollow spike 26 and inner conduit 18. Hollow spike 26 includes a longitudinal through hole 34 and protruding ridges 30. Annular cuff 28 may include a rim 28a and an annular detent 28b for receiving lower lip 42 of seal 36. Annular detent 28b snaps into an annular groove 14b in the underside of annular ring 14. Seal 36 fits into annular cuff 28 and is held in place by an internal lip 27. Spike element 24 may be formed of a thermal plastic.

Figure 4:
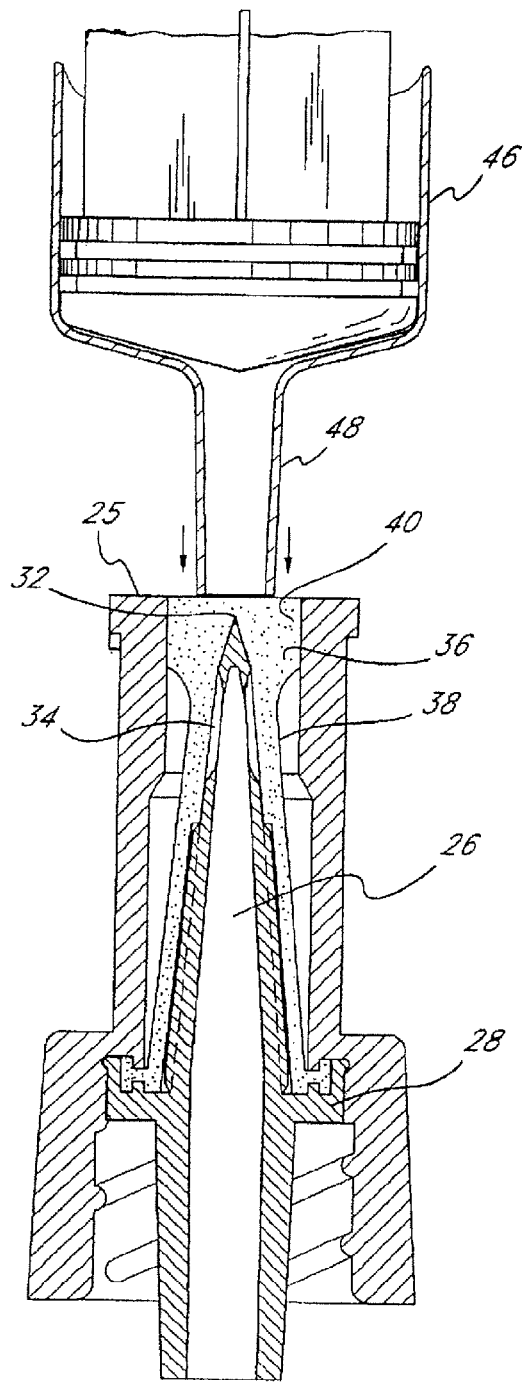
FIG. 4 is a schematic, longitudinal, cross-sectional view of the assembled valve of FIG. 1 before compressing the seal.
Figure 5:
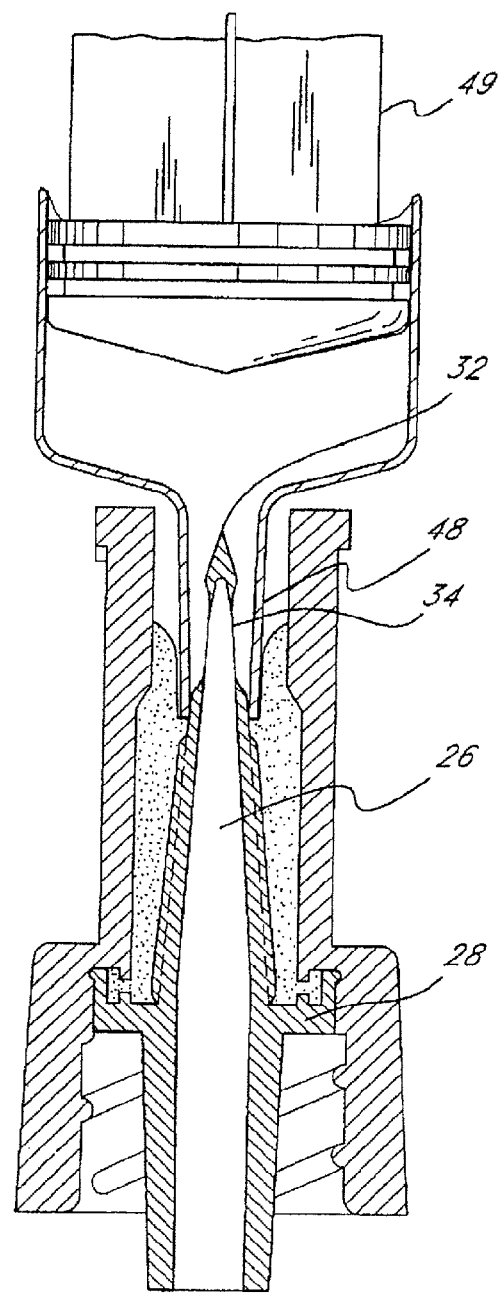
FIG. 5 is a schematic, longitudinal, cross-sectional view similar to FIG. 4 showing the valve during compression of the seal.

As shown in FIGS. 4 and 5, a syringe 46 may have its nose 48 pushed against flat top surface 40b of seal cap 40 so as to compress seal 36 until nose 48 receives the spike element 24 sufficiently deep that through hole 34 is exposed in syringe 46. A plunger 49 may then be drawn outward to draw fluid. The valve may be rotated 180 degrees such that fluid flows in the opposite direction whereby medication may be injected from the syringe.

In general, silicone such as that used for seal 36 is formed from a slurry processed at relatively low temperatures. The low temperatures at which the slurry is formed allow an antimicrobial material to be mixed in with the slurry and therefore integrated within the resulting silicone seal. Also, the outer surfaces of the thermal plastic portions (i.e., the valve body 12 and spike element 24) may be wiped, sprayed or dipped in the antimicrobial material. Thus, for example, an IV connector may be made having improved antimicrobial properties, not only on the outside of the connector, but also throughout the silicone seal.

As mentioned above, the antimicrobial material includes a silane quaternary ammonium salt. Preferred commercially available silane quaternary ammonium salts include: MicrobeCare™ XLP, which is available from MicrobeCare, LLC of Allendale, Mich.; "PROMOFRESH X 105" from Piedmont Chemical Industries I, LLC of High Point, N.C.; and AEM 5772 Antimicrobial, which is available from Aegis Environments of Midland, Mich. The antimicrobial could also be AEGIS Microbe Shield™ (from Aegis Environments, Midland, Mich.), which is a copolymer of chloropropyltrihydroxysilane and octadecylaminodimethyltrihydroxysilylpropyl ammonium chloride.

Silane quaternary ammonium salts are particularly well-suited for the antimicrobial material as they are long lasting and capable of emitting ions that aid in the destruction of a microbe. In addition, they are organofunctional silanes that include a monomer including a silane, a positively charged nitrogen molecule, and a long molecular chain. The silane bases of these monomers can covalently and permanently bond to each other and any surface. In addition, silane quaternary ammonium salts are preferable as they are substantially free from arsenic, silver, tin, heavy metals and polychlorinated phenols. Also, they are safe to apply to the patient. In addition, it not only eliminates bacteria on contact, but it remains on the treated surfaces and kills any bacteria subsequently contacting these surfaces. Such treatment preferably lasts at least one week, more preferably several months, and most preferably indefinitely.

Microbes may include bacteria, mold, mildew, algae, etc. The cell membranes of the microbes are attracted to, and then are punctured by, the long molecular chains of the monomers. As the microbes are drawn closer because of the positive-negative ion exchanges, the monomers penetrate further into the cell membranes. Once the cell membranes are penetrated deeply, they are physically ruptured by a sword-like action and then electrocuted by positively charged nitrogen molecules of the monomers, thus destroying the microbes. Thus, the microbes are eliminated without "using up" any of the antimicrobial active ingredients, which remain on and within the IV connector ready to continue protecting the patient against further microbial contamination.

If the antimicrobial material used in the silicone slurry is a 3-(trimethoxysilyl) propyldimethyloctadecyl ammonium chloride material available from MicrobeCare, LLC, it includes an active ingredient of about 43% by weight 3-(trimethoxysilyl) propyldimethyloctadecyl ammonium chloride and about 57% by weight inert ingredients.

The antimicrobial substance may then be mixed into the silicone slurry in various amounts of anywhere from about 0.001% to about 50% by weight to achieve the desired degree of antimicrobial activity while not compromising the desirable properties of the silicone seal.

To coat the thermal plastic components they may be sprayed or dipped in a solution containing the antimicrobial material. Alternatively, the antimicrobial treatment solution may be applied using wipes soaked in such a solution. Suitable wipes and solutions are disclosed in commonly-assigned U.S. Pat. No. 8,491,922, the entire disclosure of which is incorporated herein by reference. In this case, the antimicrobial material is again one of the silane quaternary ammonium salts described above.

In a preferred form, the antimicrobial treatment solution contains 30-50 percent by volume isopropyl alcohol and 50-70 percent by volume antimicrobial treatment substance, which is preferably a silane quaternary ammonium salt having an unreacted organofunctional silane. If the antimicrobial treatment solution is applied by spraying or dipping, the solution most preferably includes 50 percent by volume isopropyl alcohol and 50 percent by volume of the unreacted antimicrobial treatment substance. If the solution is applied using the wipes, the solution is preferably 30 percent by volume isopropyl alcohol and 70 percent by volume of the unreacted antimicrobial treatment substance.

The isopropyl alcohol may have a concentration of 70-90 percent by volume. By providing the unreacted organofunctional silane in isopropyl alcohol, the organofunctional silane does not react with the wipe substrates or the inside of the wipe container such that it is free to later react and permanently covalently bond with the inner and outer surfaces of the plastic components. Isopropyl alcohol is preferred as it evaporates quickly once the solution is wiped onto the treated surface to allow the unreacted organofunctional silane to more quickly react with the treated surface.

The preferred organofunctional silane quaternary ammonium salt also prevents odor, staining and product deterioration that may be associated with microbe contamination. The preferred organofunctional silane quaternary ammonium salt is also beneficial because it permanently bonds to a treated surface, covers a broad spectrum of activity with no negative effects or drawbacks, and is easily incorporated and easily verifiable.

The preferred organofunctional silane quaternary ammonium salt is designed to react and create a covalent bond with the surfaces of the plastic components. The reacted substance is held onto those surfaces until the covalent bond is broken. Tests have shown that most industrial cleaners or disinfectants will not remove the preferred antimicrobial treatment substance. The method of removal is by abrasion.

In addition to treating the plastic components of the connector, male and female luer caps that may be placed on either ends of the connector may also be treated with the antimicrobial solution. Examples of caps that may be treated include the DualCap™ caps for use on needleless luer access valves, which is available from Catheter Connections, Inc. of Salt Lake City Utah.

Although the invention is described with respect to a particular construction of a needleless IV connector shown in FIGS. 1-5, the construction thereof may vary. For example, the valve portion in the seal may include a duck bill-type valve. An example of such a needleless catheter connector with a duck bill valve is available from ICU Medical, Inc. under the trademark Neutron™. Also, the present invention may be applied to arterial connectors, catheter connectors, and dialysis connectors.

The above description is considered that of the preferred embodiments only. Modifications of the invention will occur to those skilled in the art and to those who make or use the invention. Therefore, it is understood that the embodiments shown in the drawings and described above are merely for illustrative purposes and not intended to limit the scope of the invention, which is defined by the claims as interpreted according to the principles of patent law, including the doctrine of equivalents.

What is claimed is:

1. An intravenous connector comprising:
    a valve body having an open first end configured to receive a syringe for administering medicine to a patient; and
    a silicone seal member disposed in said valve body and exposed at the open first end of said valve body configured to receive the syringe,
    wherein an antimicrobial material is incorporated on or within said silicone seal member and is coated on said valve body, and
    wherein said antimicrobial material comprises a silane quaternary ammonium salt.

2. The intravenous connector of claim 1, further comprising:
    a spike element having a tapered hollow spike terminating in a tip at a first end and having a second end configured for attaching to an intravenous tube, said spike element secured in said valve body such that said tip is disposed proximate the first end of said valve body and the second end of said spike element is located at a second end of said valve body opposite the first end of said valve body,
    wherein said antimicrobial material is coated on said spike element.

3. The intravenous connector of claim 1, wherein said silane quaternary ammonium salt includes an organofunctional silane covalently bonded to said valve body.

4. The intravenous connector of claim 1, wherein said silane quaternary ammonium salt comprises 3-(trimethoxysilyl) propyldimethyloctadecyl ammonium chloride.

5. The intravenous connector of claim 1, wherein said antimicrobial treatment is applied to said valve body as an antimicrobial treatment solution comprising said silane quaternary ammonium salt and isopropyl alcohol.

6. The intravenous connector of claim 5, wherein the antimicrobial treatment solution comprises about 30 percent to about 50 percent by volume of isopropyl alcohol at the time of application to said valve body.

7. The intravenous connector of claim 5, wherein the antimicrobial treatment solution comprises about 50 percent to about 70 percent by volume of the antimicrobial treatment substance at the time of application to said valve body.

8. The intravenous connector of claim 1, wherein said antimicrobial treatment is substantially free from arsenic, silver, tin, heavy metals and polychlorinated phenols.

9. The intravenous connector of claim 1, wherein said antimicrobial treatment is incorporated within said silicone seal member by mixing said antimicrobial treatment into a silicone slurry used to form said silicone seal member.

10. An intravenous connector comprising:
    a valve body having an open first end configured to receive a syringe for administering medicine to a patient, and a second end opposite the first end; and
    a spike element having a tapered hollow spike terminating in a tip at a first end and having a second end configured for attaching to an intravenous tube, said spike element secured in said valve body such that said tip is disposed proximate the first end of said valve body and the second end of said spike element is located at the second end of said valve body,
    a pliable seal member disposed in said valve body around said tapered hollow spike and exposed at the open first end of said valve body configured to receive the syringe,
    wherein an antimicrobial material is incorporated on or within said seal member and is coated on said valve body and said spike element, and
    wherein said antimicrobial material comprises a silane quaternary ammonium salt.

11. The intravenous connector of claim 10, wherein said silane quaternary ammonium salt includes an organofunctional silane covalently bonded to said valve body and said spike element.

12. The intravenous connector of claim 10, wherein said silane quaternary ammonium salt comprises 3-(trimethoxysilyl) propyldimethyloctadecyl ammonium chloride.

13. The intravenous connector of claim 10, wherein said antimicrobial treatment is applied to said valve body and said spike element as an antimicrobial treatment solution comprising said silane quaternary ammonium salt and isopropyl alcohol.

14. The intravenous connector of claim 10, wherein said antimicrobial treatment is substantially free from arsenic, silver, tin, heavy metals and polychlorinated phenols.

15. The intravenous connector of claim 10, wherein said pliable seal member is a silicone seal member, and said antimicrobial treatment is incorporated within said silicone seal member by mixing said antimicrobial treatment into a silicone slurry used to form said silicone seal member.

* * * * *